(12) United States Patent
Nakamura et al.

(10) Patent No.: US 7,610,427 B2
(45) Date of Patent: Oct. 27, 2009

(54) FUNCTIONAL MODULE CARD FOR TRANSFERRING DIGITAL BROADCASTING SIGNAL USING A CLOCK GENERATED BASED ON A SYNCHRONOUS SIGNAL EXTRACTED FROM A RECEIVED DATA SIGNAL

(75) Inventors: Seiji Nakamura, Minoo (JP); Isao Kato, Hirakata (JP); Tatsuya Adachi, Neyagawa (JP); Kazuya Iwata, Katano (JP)

(73) Assignee: Panasonic Corporation, Osaka (JP)

( * ) Notice: Subject to any disclaimer, the term of this patent is extended or adjusted under 35 U.S.C. 154(b) by 474 days.

(21) Appl. No.: 10/557,997

(22) PCT Filed: May 14, 2004

(86) PCT No.: PCT/JP2004/006920

§ 371 (c)(1),
(2), (4) Date: Sep. 7, 2006

(87) PCT Pub. No.: WO2004/105387

PCT Pub. Date: Dec. 2, 2004

(65) Prior Publication Data

US 2007/0177736 A1 Aug. 2, 2007

(30) Foreign Application Priority Data

May 22, 2003 (JP) .............................. 2003-145399

(51) Int. Cl.
*G06F 13/00* (2006.01)

(52) U.S. Cl. .......................... 710/301; 710/58; 710/306

(58) Field of Classification Search ......... 710/305–317, 710/58–64, 72–73
See application file for complete search history.

(56) References Cited

U.S. PATENT DOCUMENTS 6,040,851 A * 3/2000 Cheng et al. ................. 725/132

(Continued)

FOREIGN PATENT DOCUMENTS

EP 1 132 824 9/2001

(Continued)

OTHER PUBLICATIONS

Tatsuya Adachi, et al., *SDIO Card, Secure Digital Input/Output Card*, Matsushita Technical Journal, vol. 48, No. 2, pp. 124-127, Apr. 18, 2002.

(Continued)

*Primary Examiner*—Raymond N Phan
(74) *Attorney, Agent, or Firm*—Wenderoth, Lind & Ponack L.L.P.

(57) ABSTRACT

A functional module card and a host apparatus according to the present invention can constitute the digital broadcasting receiver apparatus. The functional module card includes a card controller and a tuner section. The tuner section inputs a digital broadcasting signal, generates a transport stream (referred to as a TS hereinafter) and a TS clock for transferring the TS, and directly transfers the TS and the TS clock to a decoder and descrambler of the host apparatus via a bus according to the TS clock. A data transfer method for transferring data between the card controller and the host controller of the host apparatus is a master-slave data transfer method in which the host controller operates as a master apparatus.

22 Claims, 6 Drawing Sheets

U.S. PATENT DOCUMENTS

| | | | |
|---|---|---|---|
| 6,282,412 B1 * | 8/2001 | Lyons | 455/186.1 |
| 6,651,250 B1 | 11/2003 | Takai | |
| 6,824,063 B1 * | 11/2004 | Wallace et al. | 235/487 |
| 6,922,213 B2 | 7/2005 | Yamagata | |
| 7,380,206 B1 * | 5/2008 | Usuda | 715/236 |
| 2004/0055013 A1 | 3/2004 | Ishioka et al. | |
| 2004/0225796 A1 * | 11/2004 | Hanson et al. | 710/301 |
| 2005/0146642 A1 * | 7/2005 | Fairhurst et al. | 348/552 |

FOREIGN PATENT DOCUMENTS

| | | |
|---|---|---|
| JP | 2000-115741 | 4/2000 |
| JP | 2001-197025 | 7/2001 |
| JP | 2002-135808 | 5/2002 |
| JP | 2002-218341 | 8/2002 |
| JP | 2002-300128 | 10/2002 |
| JP | 2003-51754 | 2/2003 |
| JP | 3389843 | 3/2003 |
| JP | 2003-299093 | 10/2003 |
| JP | 2004-64233 | 2/2004 |
| JP | 2004-88745 | 3/2004 |
| WO | 02/35838 | 5/2002 |

OTHER PUBLICATIONS

Hisao Sakamoto, et al., "SD Memory Card Specifications and Content Protection Technology", Matsushita Technical Journal, vol. 48, No. 2, pp. 108-114, Apr. 18, 2002.

Supplementary European Search Report (in English language) issued on Nov. 19, 2007.

Patent Cooperation Treaty (PCT) International Preliminary Report on Patentability, issued on Mar. 9, 2006.

"SD Card Specification Simplified Version of Part E1. Secure Digital Input/Output (SDIO) Card Specification", Internet Citation, [Online], Oct. 31, 2001, XP002291857.

* cited by examiner

FUNCTIONAL MODULE CARD FOR TRANSFERRING DIGITAL BROADCASTING SIGNAL USING A CLOCK GENERATED BASED ON A SYNCHRONOUS SIGNAL EXTRACTED FROM A RECEIVED DATA SIGNAL

TECHNICAL FIELD

The present invention relates to a functional module card, a host apparatus, a method for controlling the functional module card, and a method for controlling the host apparatus.

BACKGROUND ART

Recently, terrestrial digital broadcasting has started. Following the start of the terrestrial digital broadcasting, various digital broadcasting receiver apparatuses and digital broadcasting reception methods have been proposed (See, for example, Japanese patent laid-open publication Nos. 2002-300128, 2002-218341, 2002-135808 and 2001-197025, and Japanese Patent No. 3,389,843).

In the digital broadcasting receiver apparatus, a digital broadcasting reception functional module is expensive. Due to this, such an apparatus to which the digital broadcasting reception functional module can be attached as an optional unit, and a main body of which is inexpensive, is often more attractive to a user than such an expensive apparatus that contains the digital broadcasting reception functional module. The present invention realizes a functional module card that includes a digital broadcasting reception function and an inexpensive host apparatus to which the functional module card can be attached as an optional unit.

Upon realizing such a functional module card and such a host apparatus, the following two problems arise.

(i) First Problem

It is attractive to a user that the digital broadcasting reception function can be installed into a functional module card that includes a highly versatile interface, because range of user's selection of a host apparatus and an option is widened. If the functional module card that includes the highly versatile interface includes not only the digital broadcasting reception function but also the other functions, the functional module card is further attractive to the user. Conversely, if a functional module card that includes the digital broadcasting reception function can be connected to a host apparatus only via an exclusive interface, the functional module card can be attached only to a specific host apparatus, and only a specific functional module card can be attached to a host apparatus. This results in quite restrictive variations in a combination of a host apparatus and a functional module card. Such a functional module card tends to be expensive. In addition, restricted range of user's selection of a host apparatus and an option makes these products less attractive to the user.

However, generally speaking, a versatile functional module card communicates with a host apparatus by use of a master-slave communication (in which the host apparatus generates a communication clock) in which the host apparatus operates as a master apparatus and the functional module card operates as a slave apparatus. On the other hand, it is basically necessary to process and output such a digital broadcasting signal that is continuous relative to a time axis in response to such a clock that is generated from the digital broadcasting signal. Otherwise, no signal time (image (or sound) blackout or freeze) or such a state that a signal cannot be outputted and should be abandoned (image or sound skipping) may possibly occur. A method for controlling a communication clock for the versatile functional module card completely differs from a method for controlling the clock generated from the digital broadcasting signal. Accordingly, even if the digital broadcasting signal reception function is installed into a functional module card according to a prior art that includes the versatile interface, the first problem arises that the digital broadcasting signal cannot be transferred to the host apparatus in response to a correct clock.

It is an object of the present invention to provide a functional module card that includes the versatile interface and the digital broadcasting signal reception function, and transfers the digital broadcasting signal to a host apparatus in response to the correct clock, a host apparatus corresponding to the functional module card, a method for controlling the functional module card, and a method for controlling the host apparatus.

(ii) Second Problem

In the pay digital broadcasting, a broadcasting station transmits a scrambled or an encrypted digital broadcasting signal and loads such information that is necessary to descramble or decode the digital broadcasting signal to an apparatus owned by a user who pays charges. With doing so, only the user who has paid the charges can view a digital broadcasting content. However, if the functional module card includes the digital broadcasting reception function, a plurality of users can illegally view the digital broadcasting content by sharing one functional module card among the users and allowing one user to pay charges for the digital broadcasting content to the broadcasting station. Namely, a second problem arises that copyrights of digital contents transmitted from the broadcasting station cannot be protected.

It is an object of the present invention to provide a functional module card that includes a digital broadcasting reception function, that can be attached to a host apparatus as an optional unit, and that can protect copyrights of broadcast digital contents, an inexpensive host apparatus corresponding to the functional module card, a method for controlling the functional module card, and a method for controlling the host apparatus.

DISCLOSURE OF INVENTION

In order to solve the above-described problems, the present invention has the following constitutions. According to one aspect of the present invention, there is provided a functional module card that includes a communication section for communicating with a host apparatus via a plurality of connection lines and a broadcasting signal receiver section. The broadcasting signal receiver section receives a digital broadcasting signal, and generates a data signal of the digital broadcasting signal and a clock for transferring the data signal. The communication section includes the following:

a first data transfer mode for transferring data via a data bus of connection lines selected from the connection lines; and a second data transfer mode for transmitting the data signal and the clock for transferring the data signal, respectively, to the host apparatus via one connection line and via at least one another connection line other than the one connection line, the one connection line and the at least one another connection line being selected from the connection lines which transfer the data in the first data transfer mode.

The present invention realizes a functional module card that can be arbitrarily attached to a host apparatus as an optional unit, and that constitutes a system (a digital broadcasting receiver apparatus) in which a host apparatus main body is inexpensive.

The present invention realizes a functional module card that includes a versatile interface and a digital broadcasting signal reception function, and that transfers a digital broadcasting signal to a host apparatus in response to a correct clock. The present invention realizes a functional module card that can execute ordinary data transfer and digital broadcasting signal transfer between the functional module card and a host apparatus. According to the present invention, the host apparatus can correctly reproduce both of or one of a video signal and an audio signal. By transmitting a channel setting command from the host apparatus to the functional module card using the ordinary data transfer function, the host apparatus can, for example, make a channel setting and the like in a tuner section (included in the broadcasting signal receiver section) of the functional module card and the like.

The signal inputted to the functional module card is a digital broadcasting signal such as a terrestrial digital broadcasting signal, a BS digital broadcasting signal, or a CS digital broadcasting signal.

In the above-mentioned functional module card, the data signal may be a transport stream.

In the above-mentioned functional module card, the communication section preferably further transfers data to the host apparatus in the second data transfer mode, using the same transfer protocol as a transfer protocol used in the first data transfer mode, and using a data bus having a number of lines smaller than that of the first transfer mode, the data bus being selected in a further connection line other than the connection lines as used upon transferring the data signal and the clock for transferring the data signal in the second transfer mode, the further connection line being selected from the connection lines as used as the data bus in the first data transfer mode.

The present invention further realizes a functional module card that can execute an ordinary data transfer even in a mode for transmitting a digital broadcasting signal to the host apparatus.

In the above-mentioned functional module card, the communication section preferably starts communicating with the host apparatus in the first data transfer mode upon being activated, and communicates with the host apparatus after switching over to the second data transfer mode upon receiving a command for switching over to the second data transfer mode from the host apparatus.

The present invention realizes a functional module card that executes ordinary data transfer and digital broadcasting signal transfer between the functional module card and a host apparatus corresponding to the functional module card that includes the digital broadcasting signal reception function according to the present invention, and that appropriately executes the ordinary data transfer between the functional module card and a host apparatus that does not correspond to the functional module card according to the present invention.

The above-mentioned functional module card preferably further includes a buffer memory for storing the data signal received by the broadcasting signal receiver section. Responsive to a command from the host apparatus, the communication section selectively executes one of the following:

transmitting the data signal received by the broadcasting signal receiver section to the host apparatus in the second data transfer mode; and storing the data signal in the buffer memory, reading the data signal from the buffer memory, and transmitting a read data signal to the host apparatus in the first data transfer mode.

The present invention further realizes a functional module card that can transfer a digital broadcasting signal even by the ordinary data transfer.

For example, the host apparatus adjusts a rate of outputting image data to a monitor according to a time interval of clocks for transferring the transport stream.

In the above-mentioned functional module card, in the first data transfer mode, the data may be transferred via the data bus of the connection lines selected from the connection lines by a master-slave communication in which the host apparatus operates as a master apparatus and the functional module card operates as a slave apparatus.

The present invention realizes a functional module card that includes an interface for holding a versatile master-slave communication and a digital broadcasting signal reception function, and that transfers a digital broadcasting signal to a host apparatus in response to a correct clock.

According to another aspect view of the present invention, there is provided a host apparatus that includes a communication section and a broadcasting signal output section. The communication section communicates with a functional module card via a plurality of connection lines. The broadcasting signal output section inputs a data signal of a digital broadcasting signal and a clock for transferring the data signal, which are transmitted from the functional module card, performs a predetermined processing on the data signal and the clock, and outputs a resultant data signal and a resultant clock. The communication section includes the following:

a first data transfer mode for transferring data via a data bus of connection lines selected from the connection lines; and a second data transfer mode for inputting the data signal and the clock for transferring the data signal, respectively, to the host apparatus via one connection line and via at least one another connection line other than the one connection line, the one connection line and the at least one another connection line being selected from the connection lines which transfer the data in the first data transfer mode.

The present invention realizes an inexpensive host apparatus to which a functional module card that includes the digital broadcasting reception function can be attached as an optional unit. According to the present invention, the host apparatus can correctly reproduce both of or one of a video signal and an audio signal. By transmitting a channel setting command from the host apparatus to the functional module card using the ordinary data transfer function, the host apparatus can, for example, make a channel setting and the like in a tuner section of the functional module card.

The present invention realizes a host apparatus that includes a versatile interface and that receives a digital broadcasting signal from a functional module card according to the present invention in response to a correct clock. The present invention realizes a host apparatus that can execute ordinary data transfer and digital broadcasting signal reception between the host apparatus and a functional module card according to the present invention.

In the above-mentioned host apparatus, the data signal may be a transport stream.

In the above-mentioned host apparatus, the communication section preferably further inputs data from the functional module card in the second data transfer mode, using the same transfer protocol as a transfer protocol used in the first data transfer mode, and using a data bus having a number of lines smaller than that of the first transfer mode, the data bus being selected in a further connection line other than the connection lines as used upon transferring the data signal and the clock for transferring the data signal in the second transfer mode, the further connection line being selected from the connection lines as used as the data bus in the first data transfer mode.

The present invention also realizes a host apparatus that can simultaneously execute the ordinary data transfer and a mode for receiving a digital broadcasting signal from a functional module card.

In the above-mentioned host apparatus, the communication section preferably starts communicating with the functional module card in the first data transfer mode upon being activated, and when the functional module card receives the digital broadcasting signal and generates the data signal of the digital broadcasting signal and the clock for transferring the data signal, the communication section transmits a command to switch over to the second data transfer mode to the functional module card, switches over to the second data transfer mode, and thereafter communicates with the functional module card.

The present invention realizes a host apparatus that receives a digital broadcasting signal from a functional module card according to the present invention in response to a correct clock.

The host apparatus judges whether or not "the functional module card receives the digital broadcasting signal and generates the data signal of the digital broadcasting signal and the clock for transferring the data signal" typically based on functional module card identification information or functional module card functional information inputted to the host apparatus from the functional module card.

In the above-mentioned host apparatus, in the first data transfer mode, the data may be transferred via the data bus of the connection lines selected from the connection lines by a master-slave communication in which the host apparatus operates as a master apparatus and the functional module card operates as a slave apparatus.

According to a further aspect of view of the present invention, there is provided a host apparatus that includes a communication section and a broadcasting signal output section. The communication section connects to a functional module card, and receives a transport stream of a digital broadcasting signal from the functional module card. The broadcasting signal output section executes one of the following:

descrambling a scrambled transport stream of the digital broadcasting signal received by the communication section; and decoding an encrypted transport stream of the digital broadcasting signal, and outputting one of a descrambled transport stream and a decoded transport stream.

The present invention realizes a host apparatus that includes an interface for holding a versatile master-slave communication, and that receives a digital broadcasting signal from a functional module card according to the present invention in response to a correct clock.

The present invention realizes a host apparatus to which a functional module card that includes a digital broadcasting reception function can be arbitrarily attached as an optional unit, and that properly outputs a digital broadcasting signal inputted from the functional module card only if a user pays charges for the digital broadcasting to a broadcasting station.

Since functions of the digital broadcasting receiver apparatus are separately installed into the host apparatus and the functional module card, an inexpensive host apparatus can be realized. Copyrights of broadcast digital contents can be protected.

The present invention realizes a method for controlling a functional module card and a method for controlling a host apparatus that exhibit the same functions and advantageous effects as those described above.

According to the functional module card and the host apparatus according to the present invention, such a digital broadcasting receiver apparatus can be realized, that transfers a digital broadcasting signal from the functional module card to the host apparatus, and that executes ordinary data transfer between the functional module card and the host apparatus. Further, such a digital broadcasting receiver apparatus can be realized, that can arbitrarily attach the functional module card that includes a digital broadcasting reception function to a host apparatus as an optional unit, and that can protect copyrights of broadcast digital contents.

The novel features of the invention will be hereinafter fully described and particularly pointed out in the appended claims, and the configuration and details of the invention, together with other objects and features thereof, will become better understood and appreciated by reference to the following detailed description when considered in conjunction with the accompanying drawings.

It will be understood that all or part of the drawings are purely diagrammatic for illustrative purposes and do not necessarily present faithful depictions of the actual relative sizes or positions of the illustrated elements.

BEST MODE FOR CARRYING OUT THE INVENTION

Preferred embodiments that specifically show best modes for carrying out the present invention will be described hereinafter with reference to the drawings.

First Preferred Embodiment

Figure 1:
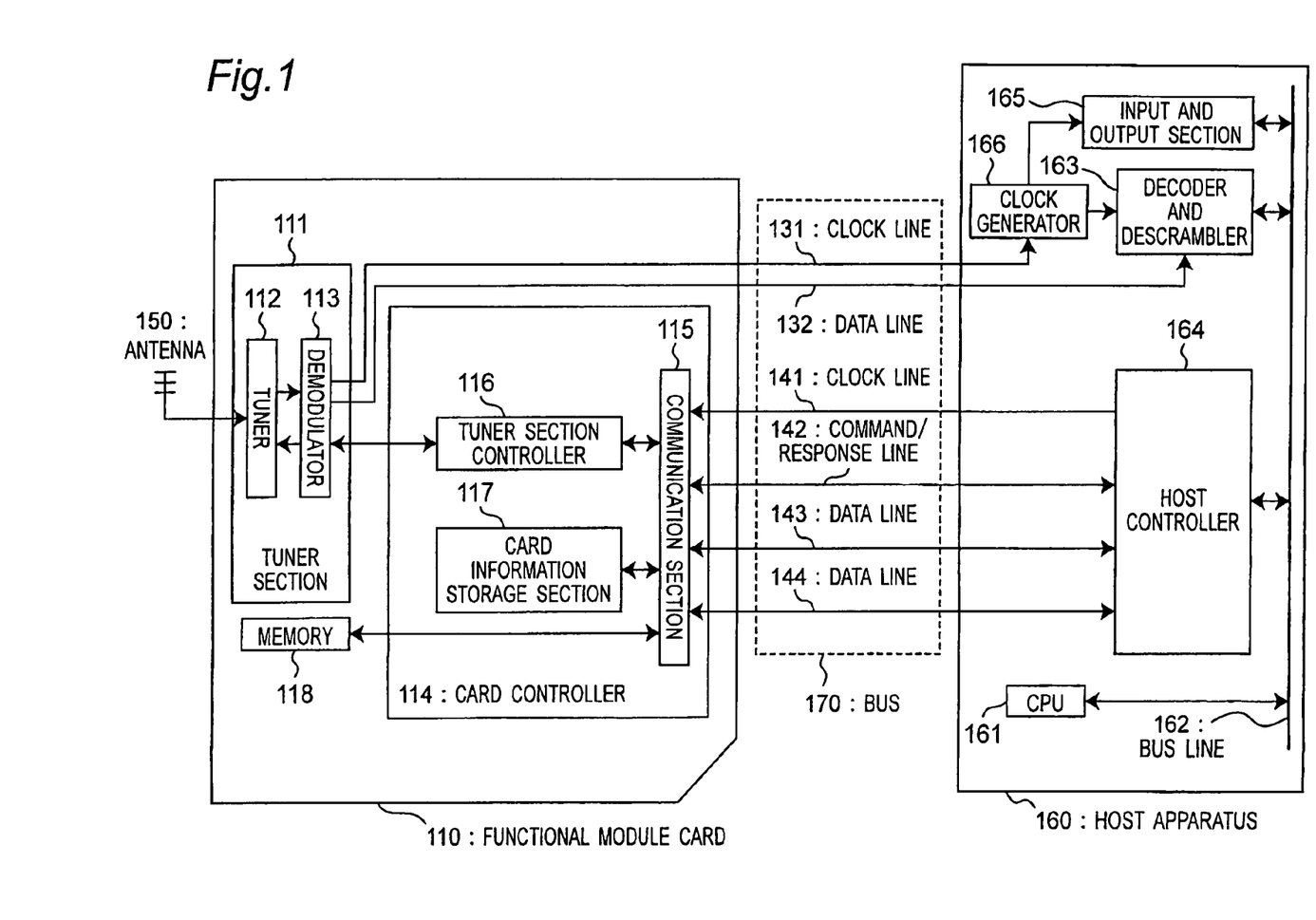
FIG. 1 is a diagram showing a configuration of a digital broadcasting receiver apparatus that includes a functional module card and a host apparatus according to a first preferred embodiment of the present invention.
Figure 2:
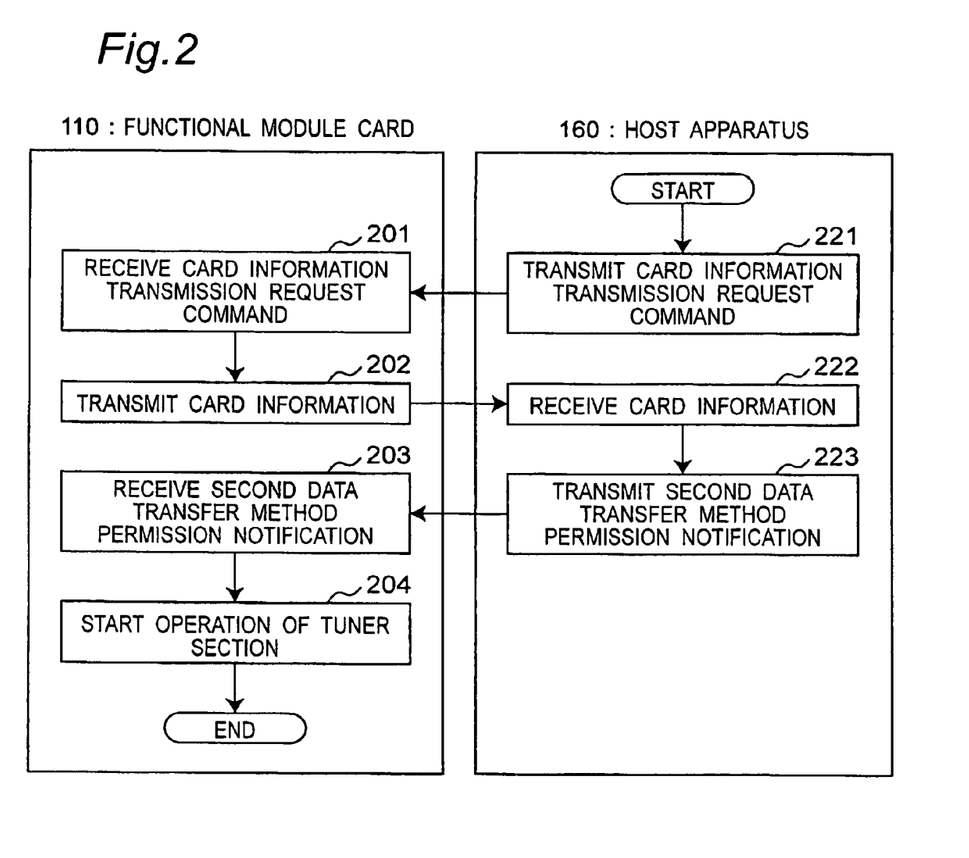
FIG. 2 is a flowchart showing a digital broadcasting receiving method (including a method for controlling the functional module card and a method for controlling the host apparatus) according to the first preferred embodiment of the present invention, in particular showing the method for controlling the functional module card and the method for controlling the host apparatus, from at the time when a user transmits a terrestrial digital broadcasting reception start command to the host apparatus to the time when a tuner section of the functional module card starts operating.
Figure 3:
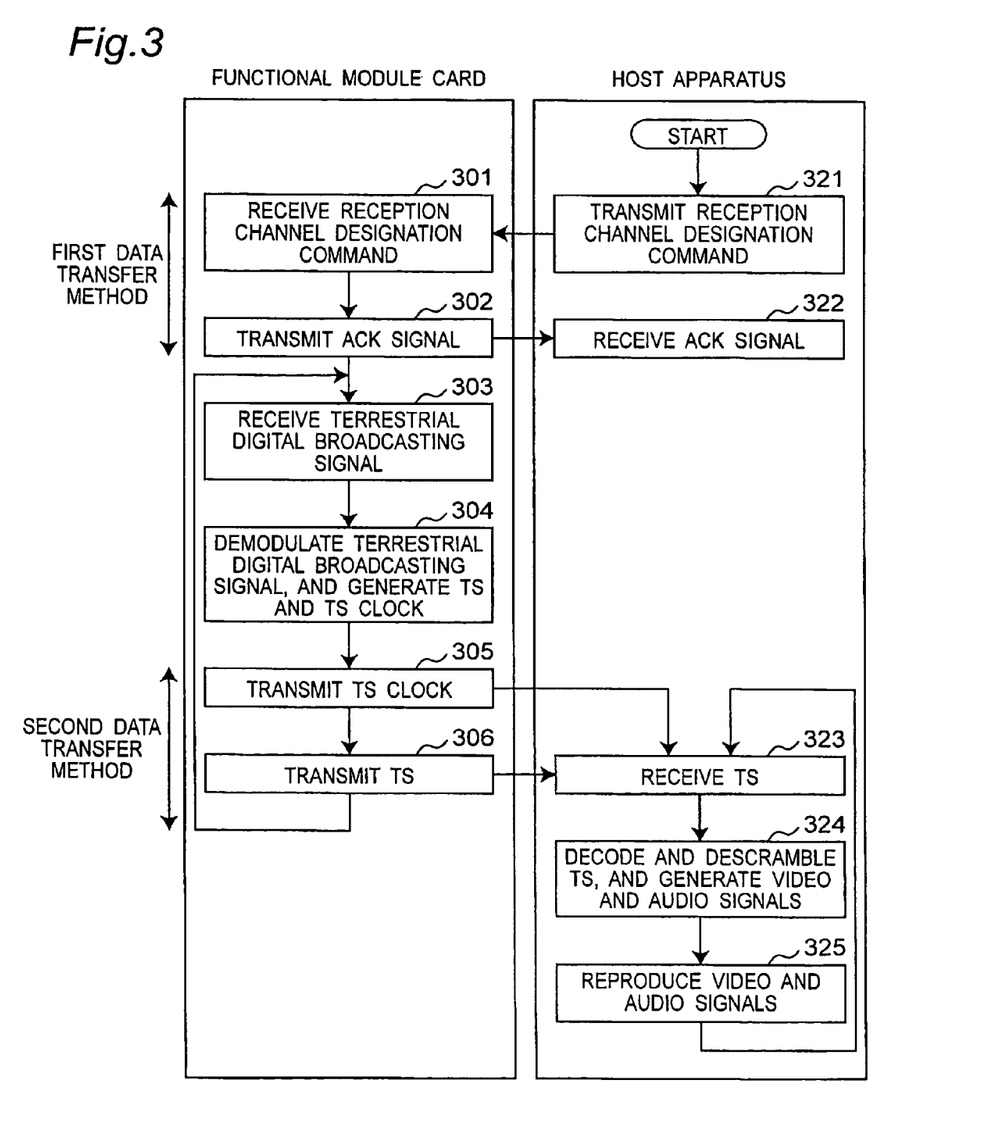
FIG. 3 is a flowchart showing a digital broadcasting receiving method (including the method for controlling the functional module card and the method for controlling the host apparatus) according to the first, a second and a third preferred embodiments of the present invention, in particular showing a method for a host apparatus 160's designating a viewing target channel to a functional module card 110 and a method for transferring a TS from the functional module card 110 to the host apparatus 160.

Referring to FIGS. 1 to 3, a functional module card, a host apparatus, a method for controlling the functional module card, and a method for controlling the host apparatus according to a first preferred embodiment of the present invention will be described.

FIG. 1 is a diagram showing a configuration of a digital broadcasting receiver apparatus that includes the functional module card and the host apparatus according to the first preferred embodiment of the present invention. Referring to FIG. 1, reference numeral 110 denotes the functional module card and reference numeral 160 denotes the host apparatus. The functional module card 110 receives a terrestrial digital broadcasting signal, and transfers a transport stream (referred to as a "TS" hereinafter) of a broadcasting signal (including video and audio signals) on a channel selected by a tuner 112 to the host apparatus 160. The host apparatus 160 decodes and descrambles an inputted TS and outputs the video and audio signals of the terrestrial digital broadcasting.

The functional module card 110 includes an antenna 150, a tuner section 111, a card controller 114, and a memory 118. The tuner section 111 includes the tuner 112 and a demodulator 113. The card controller 114 includes a communication section 115, a tuner section controller 116, and a card information storage section 117. The host apparatus 160 includes a CPU (Central Processing Unit) 161, a bus line 162, a decoder and descrambler 163, a host controller 164, an input and output section 165, and a clock generator 166.

The host apparatus 160 includes a card slot (not shown) to which the functional module card 110 can be attached. A connector (not shown) provided to the card slot of the host apparatus 160 is connected to a connector (not shown) of the functional module card 110 that is attached to the card slot. Via the connectors, the host apparatus 160 outputs electric power, a control command, data and the like to the functional module card 110, and inputs a video signal, an audio signal, data and the like of a moving image outputted from the functional module card 110. The host apparatus 160 is a PDA (Personal Digital Assistant). Alternatively, the host apparatus 160 may be the other apparatus (such as a notebook type personal computer or a mobile telephone).

The host apparatus 160 enables any one of not only the functional module card 110 but also various kinds of other functional module cards (such as a functional module card including only a memory function and a functional module card including a memory function and the other function (e.g., a radio communication function)) to be attached to the card slot (including the connector provided in the card slot) and to operate.

In the first preferred embodiment, the functional module card 110 is an SD card (registered trademark). The functional module card 110 may be an arbitrary versatile functional module card such as an SD card, an IC card or a memory stick (registered trademark). By attaching the functional module card 110 to the host apparatus 160, such a function that is installed into the functional module card 110 can be added to the host apparatus 160. In the first preferred embodiment, the functional module card 110 includes a terrestrial digital broadcasting signal reception function and a memory function, and these functions are added to the host apparatus 160.

The input and output section 165 of the host apparatus 160 receives a command from an external apparatus. For example, a user inputs a command such as a terrestrial digital broadcasting reception start command or a reception channel designation command to the host apparatus 160 via the input and output section 165 (that includes an operation section). Further, the input and output section 165 outputs the video signal and the audio signal to a display and loudspeakers, which is either an external apparatus connected to the host apparatus 160 or is included in the host apparatus 160. A method for outputting the video and audio signals via the input and output section 165 will be described later.

The CPU 161 controls internal operations (that includes an operation of the host apparatus 160 as the PDA and operations for controlling the decoder and descrambler 163 and the like) of the host apparatus 160. In addition, the CPU 161 transmits a command to perform each operation to the functional module card 110 and controls a communication between the host controller 164 and the communication section 115.

The host apparatus 160 can store such data, that is generated internally or inputted from the external apparatus via the input and output section 165, in the memory 118 of the functional module card 110, or can process and output data read out from the memory 118.

The functional module card 110 and the host apparatus 160 are connected to each other via a bus 170. The bus 170 includes a clock line 131 and a data line 132 for executing communications between the tuner section 111 and the clock generator 166, and between the tuner section 111 and decoder and descrambler 163. The bus further includes a clock line 141, data lines 143 and 144, and a command/response line 142 for executing the communication between the host controller 164 and the communication section 115. A power source line for supplying the electric power from the host apparatus 160 to the functional module card 110 and a ground line are included in connection lines (not shown) for connecting the functional module card 110 to the host apparatus 160. The functional module card 110 operates when the electric power is supplied to the functional module card 110 from the host apparatus 160.

The host controller 164 and the communication section 115 are connected to each other via the clock line 141, the data lines 143 and 144, and the command/response line 142. A master-slave communication (referred to as a "first data transfer method" hereinafter), in which the host apparatus 160 operates as a master apparatus and the functional module card 110 operates a slave apparatus, is held between the host controller 164 and the communication section 115. With the first data transfer method, a synchronous communication for bidirectionally transmitting commands and responses (transmitted via the command/response line 142) and data (transmitted via the command/response line 142 or the data lines 143 and 144 depending on types of the data) in response to a clock (referred to as a "host clock" hereinafter, which is transmitted via the clock line 141) outputted from the host controller 164 is executed. The host controller 164 transmits a command (or a command and data) to the communication section 115, and the communication section 115 transmits a response (or a response and data) to the host controller 164 in response to the command. A mode of transferring data using only the first data transfer method will be referred to as a "first data transfer mode".

The tuner section controller 116 controls the tuner 112 so as to start receiving signals and makes a reception channel setting and the like in response to the command such as the terrestrial digital broadcasting reception start command or the reception channel designation command transmitted from the host controller 164 to the communication section 115.

The tuner 112 receives a terrestrial digital broadcasting signal on the selected channel in response to the command transmitted from the tuner controller 116. The demodulator 113 of the tuner section 111 demodulates a terrestrial digital broadcasting signal received by the tuner 112 to a baseband signal, and generates a TS of the baseband signal and a clock (referred to as a "TS clock" hereinafter) for transferring data of the TS.

The demodulator 113 is connected to the decoder and descrambler 163 via the data line 132. The demodulator 113 is connected to the clock generator 166 via the clock line 131. The demodulator 113 unidirectionally transfers the TS clock and the TS (including the video and audio signals), as continuous signals, to the clock generator 166 and the decoder and descrambler 163 via clock line 131 and the data line 132 (this transfer method will be referred to as a "second data transfer method" hereinafter). With the second data transfer method, a synchronous communication using the TS clock is executed. Further, a mode of transferring data using the second data transfer method will be referred to as a "second data transfer mode" (the second data transfer mode includes such a data transfer that the first data transfer method and the second data transfer method are used simultaneously).

The clock generator 166 inputs the TS clock and divides the TS clock by N. Further, the clock generator 166 transfers the TS clock to the decoder and descrambler 163, and transfers a TS clock divided by N to the input and output section 165.

The TS clock and the TS are inputted to the decoder and descrambler 163. The decoder and descrambler 163 of the host apparatus 160 inputs the TS in response to the TS clock, and decodes and descrambles the terrestrial digital broadcasting signal.

The input and output section 165 outputs the video and audio signals outputted from the decoder and descrambler 163 to the display and the loudspeakers (which are either connected to the host apparatus 160 as external apparatuses or included in the host apparatus 160) at a timing of the TS clock divided by N.

The card information storage section 117 stores information (referred to as "card information") on the functions of the functional module card 110 including information that the functional module card 110 can receive the terrestrial digital broadcasting signal, transmit the TS of the terrestrial digital broadcasting signal by use of the second data transfer method, and transmit and receive data signals by use of the first data transfer method.

The memory 118 is a nonvolatile memory (which is a flash memory in the first preferred embodiment). Data transmitted from the host controller 164 of the host apparatus 160 to the communication section 115 is written into the memory 118. In addition, data read out from the memory 118 is transmitted to the host apparatus 160 via the communication section 115 and the host controller 164.

In the functional module card 110, an output buffer (not shown) of the tuner section 111 for outputting the TS and the TS clock, and the communication section 115 constitute a communication section of the functional module card 110. The tuner 112 and the demodulator 113 of the tuner section 11 constitute a broadcasting signal reception section.

In the host apparatus 160, an input buffer (not shown) of the decoder and descrambler 163, an input buffer (not shown) of the clock generator 166, and a communication interface of the host controller 164 for communicating with the communication section 115 constitute a communication section of the host apparatus 160. The decoder and descrambler 163, the clock generator 166, and an output interface (not shown) of the input and output section 165 for outputting the video and audio signals constitute a broadcasting signal output section of the host apparatus 160.

Referring to FIGS. 2 and 3, the method for controlling the functional module card and the method for controlling the host apparatus according to the first preferred embodiment of the present invention will be described. FIG. 2 is a flowchart showing a digital broadcasting receiving method (including the method for controlling the functional module card and the method for controlling the host apparatus) according to the first preferred embodiment of the present invention, in particular showing the method for controlling the functional module 110 card and the method for controlling the host apparatus 160, from at the time when a user transmits the terrestrial digital broadcasting reception start command to the host apparatus 160 to the time when a tuner section 111 of the functional module 110 card starts operating.

The user inputs the terrestrial digital broadcasting reception start command to the input and output section 165. The host controller 164 receives the terrestrial digital broadcasting reception start command from the input and output section 165 via the bus line 162. In step 221, the host controller 164 transmits a card information transmission request command to the communication section 115 via the command/response line 142. During transmission of the command or data or during reception of the response or data, the host controller 164 outputs the host clock via the clock line 141.

The communication section 115 of the functional module card 110 receives the card information transmission request command (step 201). The communication section 115 reads out the card information including information that the functional module card 110 can receive the terrestrial digital broadcasting signal and transmit the TS of the terrestrial digital broadcasting signal by use of the second data transfer method from the card information storage section 117, and transmits the card information to the host controller 164 via the data line 143 or the data lines 143 and 144 (step 202). The host controller 164 receives the card information in step 222, and transmits a notification of permitting the functional module card 110 to transfer data by use of the second data transfer method (second data transfer method permission notification) to the communication section 115 of the functional module card 110 via the command/response line 142 in step 223. In step 203, the communication section 115 receives the second data transfer method permission notification. The communication section 115 transmits a command for the tuner section 111 to start receiving signals (signal reception start command) to the tuner section controller 116. The tuner section controller 116 controls the tuner section 111 so as to start operating (step 204).

FIG. 3 is a flowchart showing the digital broadcasting receiving method (including the method for controlling the functional module card and the method for controlling the host apparatus) according to the first preferred embodiment of the present invention, in particular showing a method for the host apparatus 160's designating a viewing target channel to the functional module card 110 and a method for transferring the TS from the functional module card 110 to the host apparatus 160.

The user designates the viewing target channel via the input and output section 165 of the host apparatus 160. The input and output section 165 instructs the host controller 164 to transmit the reception channel designation command. The host controller 164 transmits the reception channel designation command to the communication section 115 of the functional module card 110 via the command/response line 142, and transmits a reception channel value to the communication section 115 via the data line 143 or the data lines 143 and 144 (step 321) (the reception channel designation command and the channel value will be collectively referred to as a "reception channel designation command" hereinafter). The host controller 164 outputs the host clock from the clock line 141 during transmission of the command or data or during reception of the response or data. The communication section 115 of the functional module card 110 receives the reception channel designation command (step 301). The communication section 115 transmits an ACK signal to the host controller 164 via the command/response line 142 (step 302). The host controller 164 receives the ACK signal (step 322).

Data transmission in steps 301, 302, and 321 to 322 is executed by use of the first data transfer method.

The communication section 115 transmits the channel designation command to the tuner section 111 via the tuner section controller 116. In step 303, the tuner 112 receives a terrestrial digital broadcasting signal on the designated channel with the antenna 150, and inputs the terrestrial digital broadcasting signal on the designated channel to the demodulator 113. The demodulator 113 demodulates the terrestrial digital broadcasting signal to the baseband signal, generates the TS, and generates the TS clock based on a synchronous signal extracted from the TS (step 304). In step 305, the demodulator 113 transmits the TS clock to the clock generator 166 of the host apparatus 160 via the clock line 131. The clock generator 166 transfers the received TS clock to the decoder and descrambler 163 as it is. In step 306, the demodulator 113 transmits the TS to the decoder and descrambler 163 of the host apparatus 160 via the data line 132, and then the control flow returns to step 303. The TS is transferred synchronously with not the host clock but the TS clock generated by the demodulator 113. In step 323, the decoder and descrambler 163 receives the TS and the TS clock. Data transfer in steps 305, 306, and 323 is executed by use of the second data transfer method.

The decoder and descrambler 163 decodes and descrambles the TS, generates the video and audio signals, and transmits generated video and audio signals to the input and output section 165 via the bus line 162 (step 324). The input and output section 165 receives the video and audio signals, and outputs received video and audio signals to the display and the loudspeakers at a timing of the TS clock divided by N. The video and audio signals are reproduced (step 325). Thereafter, the control flow returns to step 323.

The host clock and the TS clock are completely different from each other, and they are not in synchronization with each other. According to the first preferred embodiment, the TS is transferred in response to the TS clock generated from the TS via the two signal lines (the clock line 131 and the data line 132), that are different from the signal lines (the command/response line 142, the clock line 141, and the data lines 143 and 144) used in an ordinary master-slave communication. Accordingly, the decoder and descrambler 163 of the host apparatus 160 can completely synchronizes with the digital broadcasting signal received by the functional module card 110. The host apparatus 160 can reproduce the video and audio signals correctly without any discontinuity (e.g., image (or sound) blackout, freeze or skipping).

The host apparatus 160 and the functional module card 110 can execute transmission of a channel setting operation command and the like by use of the first data transfer method in parallel with transmission of the TS by use of the second data transfer method. While the functional module card 110 transmits the TS to the host apparatus 160, the host apparatus 160 can receive the reception channel designation command from the user and transmit a received command to the functional module card 110. In addition, the host apparatus 160 can write or read out data into or from the memory 118 regardless of whether or not the functional module card 110 transmits the TS to the host apparatus 160.

The data transfer via the one data line 143 or the two data lines 143 and 144 using the first data transfer method is executed according to the same data transfer protocol specified in versatile functional module cards. Due to this, the functional module card 110 can execute functions (e.g., the function of storing data to the memory 118) other than at least the digital broadcasting reception function, even if the functional module card 110 is attached not to the host apparatus 160 according to the present invention but to the host apparatus according to the prior art. The host apparatus 160 can fulfill the functions of not only the functional module card 110 according to the present invention but also the functional module card according to the prior art (which cannot output the TS and the TS clock), connected thereto.

According to the first preferred embodiment, the functional module card 110, which is the SD card, and the host apparatus 160 execute the data transfer by use of the first data transfer method according to a data transfer protocol specified in ordinary SD cards (See, for example, Matsushita Technical Journal (Japan), 2002, Volume 48, 3rd Issue, p. 110). According to the data transfer protocol specified in ordinary SD cards, data transfer in a one-bit mode using one data line or data transfer in a four-bit mode using four data lines can be executed. The first data transfer method according to the first preferred embodiment is the one-bit mode data transfer in which data is transferred via any one of the data lines 143 and 144.

In the first preferred embodiment, the tuner section 111 and the decoder and descrambler 163 are separately installed into the functional module card 110 and the host apparatus 160, respectively. A scrambled TS is outputted from the functional module card 110 via the bus 170. The TS can be descrambled only by the host apparatus 160 that holds correct scrambling information. Due to this, even if the functional module card 110, for example, is attached to a host apparatus of a user who does not subscribe to terrestrial digital broadcasting viewing, the user's host apparatus cannot correctly descramble the TS. Accordingly, copyrights of digital contents that are included in the TS is protected.

According to the first preferred embodiment, only minimum functions for viewing terrestrial digital broadcasting contents are installed into the host apparatus 160. The other functions are installed into the functional module card 110. By installing the functional module card 160 to the host apparatus 160, the functions of the host apparatus 160 can be extended. Accordingly, as compared with the host apparatus into which all the functions necessary to receive terrestrial digital broadcasting signal are installed, the host apparatus 160 according to the present invention can be provided at lower cost. If the user who purchased the host apparatus 160 intends to extend the functions of the host apparatus 160 after the purchase, the user may attach a functional module card into which functions to be extended are installed to the card slot of the host apparatus 160. If the broadcasting standards of digital broadcasting signals on reception channels are different from each other, the user may attach such a functional module card that includes a tuner corresponding to specifications of a digital broadcasting signal on a user's desired reception channel, to the card slot.

Second Preferred Embodiment

Figure 4:
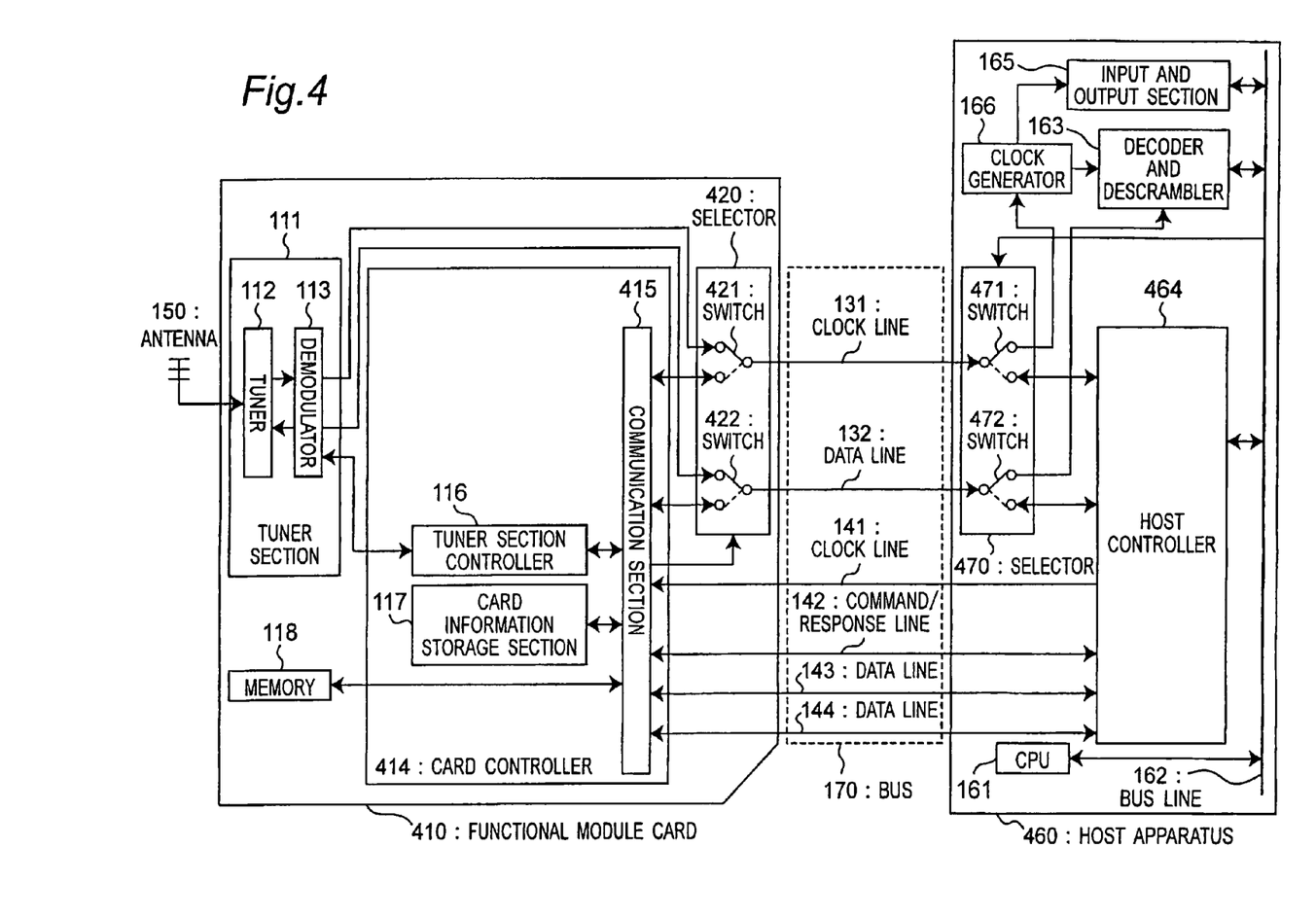
FIG. 4 is a diagram showing a configuration of a digital broadcasting receiver apparatus that includes a functional module card and a host apparatus according to the second preferred embodiment of the present invention.
Figure 5:
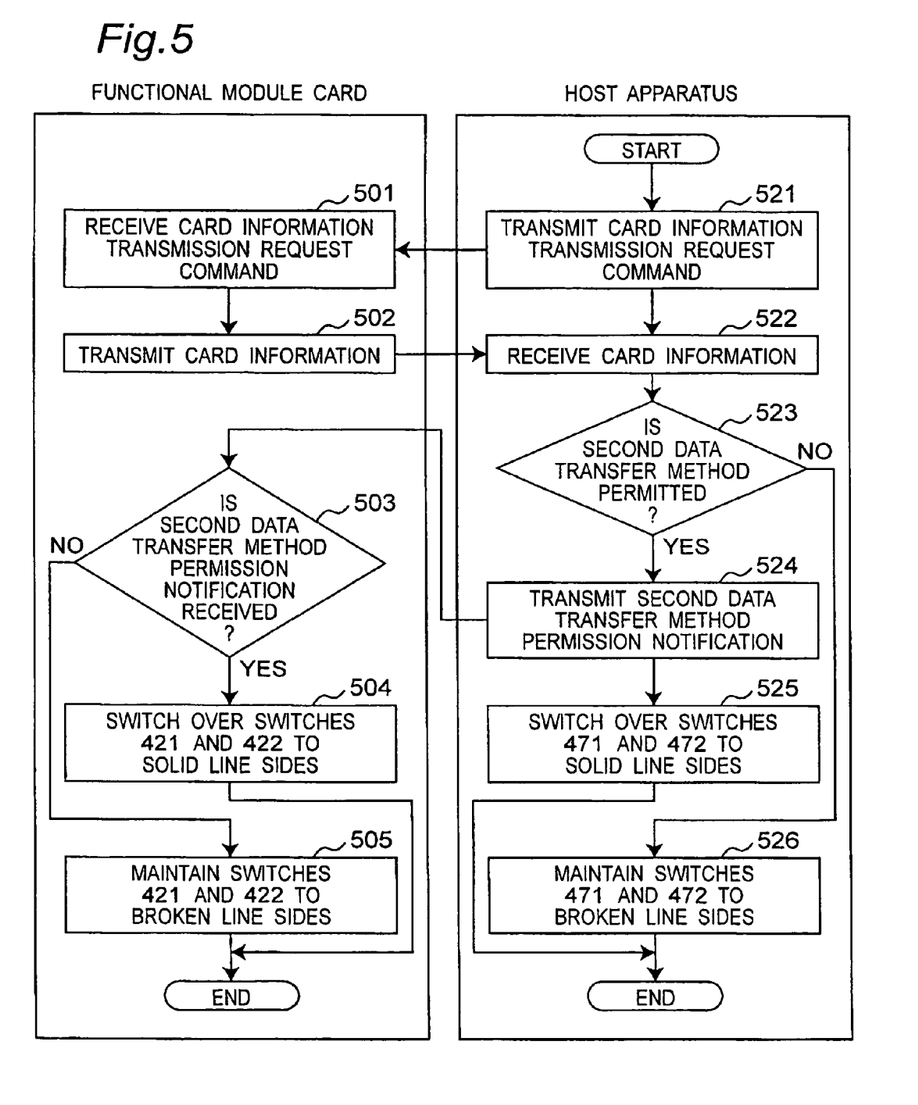
FIG. 5 is a flowchart showing a digital broadcasting receiving method (including a method for controlling the functional module card and a method for controlling the host apparatus) according to the second and the third preferred embodiments of the present invention, in particular showing the method for controlling the functional module card and the method for controlling the host apparatus, from at the time when the user transmits a terrestrial digital broadcasting reception start command to the host apparatus to the time when selectors are switched over.

Referring to FIGS. 3, 4 and 5, a functional module card, a host apparatus, a method for controlling the functional module card, and a method for controlling the host apparatus according to a second preferred embodiment of the present invention will be described.

FIG. 4 is a diagram showing a configuration of a digital broadcasting receiver apparatus that includes the functional module card and the host apparatus according to the second preferred embodiment of the present invention. Referring to FIG. 4, reference numeral 410 denotes a functional module card and reference numeral 460 denotes a host apparatus. The functional module card 410 according to the second preferred embodiment has such a configuration that the card controller 114 and the communication section 115 of the functional module card 110 according to the first preferred embodiment (shown in FIG. 1) are replaced with a card controller 414 and a communication section 415, respectively, and a selector 420 is added. The selector 420 includes switches 421 and 422. The host apparatus 460 according to the second preferred embodiment has such a configuration that the host controller 164 of the host apparatus 160 according to the first preferred embodiment (shown in FIG. 1) is replaced with a host controller 464, and a selector 470 is added. The selector 470 includes switches 471 and 472.

The functional module card 410 and the host apparatus 460 are connected to each other via a bus 170. The bus 170 includes a clock line 131, a data line 132, a clock line 141, data lines 143 and 144, and a command/response line 142. The clock line 131 is often used as a data line.

In the digital broadcasting receiver apparatus shown in FIG. 4, components as used commonly to the digital broadcasting receiver apparatuses shown in FIGS. 1 and 4 are denoted by the same reference numerals, respectively, and they will not be described.

The communication section 415 of the functional module card 410 and the host apparatus 460 execute data transfer by use of the first data transfer method as described in the first preferred embodiment in response to a clock (a host clock) of the host apparatus 460. The communication section 415 of the card controller 414 and the host controller 464 of the host apparatus 460 execute data transfer by use of the first data transfer method via the clock line 141, the command/response line 142, and one data line 143 (or two data lines 143 and 144 or four data lines 131 (note that the clock line 131 is used as a data line), 132, 143 and 144).

(i) When the switches 421, 422, 471 and 472 are switched over to broken line sides thereof, respectively (referred to as a "first data transfer mode"), the functional module card 410 does not transfer a TS and a TS clock to the host apparatus 460. In this case, the clock line 131 and the data line 132 are used as data lines for the data transfer between the host controller 464 and the communication section 415. The communication section 415 of the card controller 414 and the host controller 464 of the host apparatus 460 execute data transfer by use of the first data transfer method via the clock line 141, the command/response line 142, and the four data lines 131, 132, 143 and 144 (or one data line 143 or two data lines 143 and 144 instead of using the four data lines). For example, data is transferred from the memory 118 to the host apparatus 460 via the data lines. Since the data bus 170 has a maximum bus width of four bits, a large amount of data can be transmitted at high rate.

(ii) Data transfer method ("second data transfer method") that is used when the switches 421, 422, 471 and 472 are switched over to solid line sides thereof, respectively (referred to as a "second data transfer mode") will be described. The TS clock is transferred from a demodulator 113 of the functional module card 410 to a decoder and descrambler 163 via the clock line 131 and a clock generator 166 of the host apparatus 460 (note that a signal transferred from the clock generator 166 to the decoder and descrambler 163 is the TS clock itself). The TS is transferred directly from the demodulator 113 to the decoder and descrambler 163 via the data line 132. With the second data transfer method, a synchronous communication using the TS clock is executed.

In this case, the communication section 415 of the card controller 414 and the host controller 464 of the host apparatus 460 execute data transfer by use of the first data transfer method via the clock line 141, the command/response line 142, and one data line 143 (or two data lines 143 and 144). The data transfer using the first data transfer method can be executed even in parallel with execution of the second data transfer method (the second data transfer mode).

In the functional module card 410, an output buffer (not shown) of the tuner section 111 for outputting the TS and the TS clock, the communication section 415, and the selector 420 constitute a communication unit of the functional module card 410. The tuner 112 and the demodulator 113 of the tuner section 111 constitute a broadcasting signal reception unit.

In the host apparatus 460, an input buffer (not shown) of the decoder and descrambler 163, an input buffer (not shown) of the clock generator 166, a communication interface of the host controller 464 for the communication with the communication section 415, and the selector 470 constitute a communication section of the host apparatus 460. The decoder and descrambler 163, an output interface (not shown) of the input and output section 165 for outputting the video and audio signals, and the clock generator 166 constitute a broadcasting signal output section of the host apparatus 460.

Referring to FIGS. 3 and 5, the method for controlling the functional module card and the method for controlling the host apparatus according to the second preferred embodiment of the present invention will be described. FIG. 5 is a flowchart showing a digital broadcasting receiving method (including the method for controlling the functional module card and the method for controlling the host apparatus) according to the second preferred embodiment of the present invention, in particular showing the method for controlling the functional module card 410 and the method for controlling the host apparatus 460, from at the time when the user transmits a terrestrial digital broadcasting reception start command to the host apparatus 460 to the time when selectors 420 and 470 (the switches 421, 422, 471, and 472) are switched over. In the host apparatus 460 and the functional module card 410, the switches 471 and 472 and the switches 421 and 422 are switched over to broken line sides thereof, respectively, when a power is turned on. By so setting, when the power is turned on, the host apparatus 460 and the functional module card 410 include the same interface (the first data transfer mode) as that of the host apparatus and the functional module card according to the prior art. Therefore, the host apparatus 460 and the functional module card 410 are completely compatible with the host apparatus and the functional module card according to the prior art, respectively, on the interface. The user inputs a terrestrial digital broadcasting reception start command to the input and output section 165. The host controller 464 receives the terrestrial digital broadcasting reception start command from the input and output section 165 via the bus line 162. In step 521, the host controller 464 transmits a card information transmission request command to the communication section 415 via the command/response line 142. During transmission of a command or data or during reception of a response or data, the host controller 464 outputs the host clock via the clock line 141.

The communication section 415 of the functional module card 410 receives the card information transmission request command (step 501). The card information storage section 117 stores information (referred to as "card information") including information on a data transfer method for the TS of the terrestrial digital broadcasting signal. In the second preferred embodiment, the card information storage section 117 stores the card information on the functions of the functional module card 410 including information that the functional module card 410 can receive a terrestrial digital broadcasting signal, transmit the TS of the terrestrial digital broadcasting signal by use of the second data transfer method, and transmit and receive data signals by use of the first data transfer method. The communication section 415 reads out the card information from the card information storage section 117, and transmits the card information to the host controller 464 via the data line 143, the data lines 143 and 144, or the four data lines 131, 132, 143, and 144 (step 502). The host controller 464 receives the card information in step 522. In step 523, responsive to the card information, a CPU 161 judges whether or not a data transfer using the second data transfer method is permitted.

When the functional module card 410 includes a data transfer function for transferring data using the second data transfer method, and furthermore the memory 118 is not transferring a large amount of data to or from the host apparatus 460, the CPU 161 permits the data transfer using the second data transfer method. When the CPU 161 permits the data transfer using the second data transfer method, the control flow goes from step 523 to step 524. The host controller 464 transmits a notification of permitting TS transfer using the second data transfer method (second data transfer method permission notification) to the communication section 415 via the command/response line 142. The CPU 161 switches over the switches 471 and 472 of the selector 470 to the solid line sides thereof, respectively. In step 503, the communication section 415 receives the second data transfer method permission notification. The communication section 415 switches over the switches 421 and 422 of the selector 420 to the solid line sides thereof, respectively (step 504). The communication section 415 transmits a command for the tuner section 111 to start receiving signals ("signal reception start command") to the tuner section controller 116. The tuner section controller 116 controls the tuner section 111 so as to start operating. The tuner section 111 outputs the TS clock and the TS to the clock line 131 and the data line 132, respectively. The tuner section 111 transmits the TS to the decoder and descrambler 163 of the host apparatus 460 by use of the second data transfer method (the second data transfer mode).

When the functional module card 410 does not include the data transfer function for transferring data using the second data transfer method or when the memory 118 is quickly transferring a large amount of data to or from the host apparatus 460, the CPU 161 does not permit the data transfer using the second data transfer method. When the CPU 161 does not permit the data transfer using the second data transfer method, the control flow goes from step 523 to step 526. The CPU 161 maintains the switches 471 and 472 of the selector 470 to the broken line sides thereof, respectively (step 526). In step 503, the communication section 415 does not receive the second data transfer method permission notification, and the control flow goes to step 505. In step 505, the switches 421 and 422 of the selector 420 are maintained to the broken line sides thereof, respectively.

When the host apparatus 460 permits the transfer of the TS using the second data transfer method, the transfer of the TS from the functional module card 410 to the host apparatus 460 is executed by the same method as that according to the first preferred embodiment (shown in FIG. 3). FIG. 3 has been already described above.

When the host apparatus 460 does not permit the transfer of the TS using the second data transfer method, the transfer of the TS from the functional module card 410 to the host apparatus 460 is not executed. The clock line 131 and the data line 132 are used as the data lines for the first data transfer method. The first data transfer method according to the second preferred embodiment is the same as that of the first data transfer method according to the first preferred embodiment except that the data can be transmitted via a maximum of four data lines. The bus operating in the first data transfer method is used when data other than the TS (e.g., such data that is stored in the memory 118 or the card information storage section 117 in the second preferred embodiment) is transferred between the host apparatus 460 and the functional module card 410.

In the second preferred embodiment, the data transfer via the four data lines 131, 132, 143 and 144 in the first data transfer mode (using the first data transfer method) and the data transfer via the one data line (143 or 144) in the second data transfer mode (using the first data transfer method) are executed according to the data transfer protocols (as already described in the first preferred embodiment) specified in ordinary SD cards, respectively. Namely, with the first data transfer method in the first data transfer mode, data is transferred in the four-bit mode. With the first data transfer method in the second data transfer mode, data is transferred in the one-bit mode. Due to this, the functional module card 410 can execute functions (e.g., the function of storing data to the memory 118) other than at least the digital broadcasting reception function, even if the functional module card 410 is attached not to the host apparatus 460 according to the present invention but to the host apparatus according to the prior art. The host apparatus 460 can fulfill the functions of not only the functional module card 410 according to the present invention but also the functional module card according to the prior art (which cannot output the TS and the TS clock), connected thereto.

Third Preferred Embodiment

Figure 6:
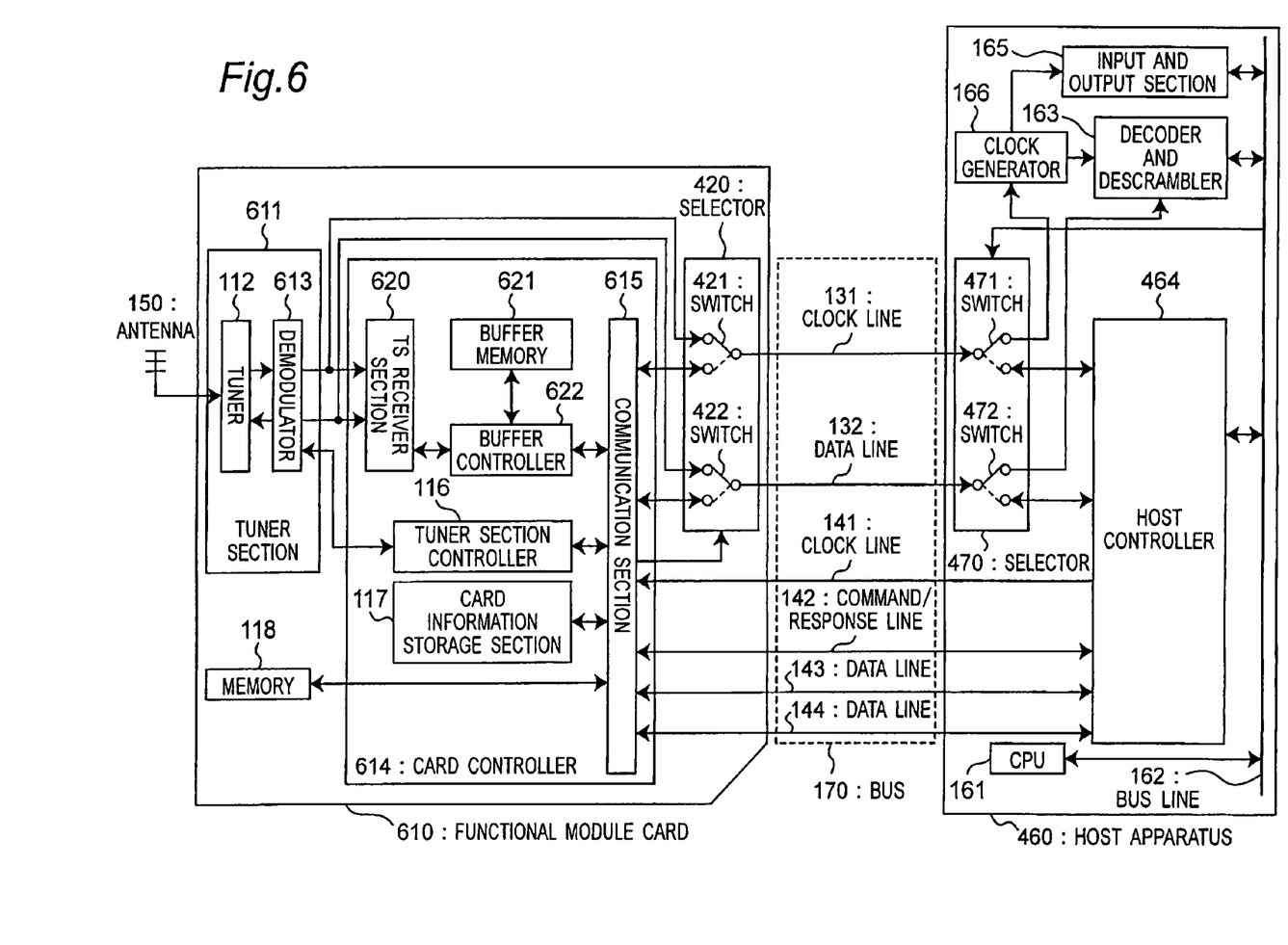
FIG. 6 is a diagram showing a configuration of a digital broadcasting receiver apparatus that includes a functional module card and a host apparatus according to the third preferred embodiment of the present invention.

When the functional module card 110 according to the first preferred embodiment or the functional module card 410 according to the second preferred embodiment is used in combination with such a host apparatus that cannot transfer the TS by use of the second data transfer method or such a host apparatus that does not permit transferring the TS using the second data transfer method, the user is unable to view terrestrial digital broadcasting contents. A functional module card according to a third preferred embodiment is intended to solve this problem. Referring to FIGS. 3, 5 and 6, the functional module card, a host apparatus, a method for controlling the functional module card, and a method for controlling the host apparatus according to the third preferred embodiment of the present invention will be described.

FIG. 6 is a diagram showing a configuration of a digital broadcasting receiver apparatus that includes the functional module card and the host apparatus according to the third preferred embodiment of the present invention. Referring to FIG. 6, reference numeral 610 denotes the functional module card and reference numeral 460 denotes the host apparatus. The digital broadcasting receiver apparatus shown in FIG. 6 has such a configuration that the functional module card 410 in the digital broadcasting receiver apparatus shown in FIG. 4 is replaced with a functional module card 610. Since the host apparatus 460 is the same as the host apparatus 460 according to the second preferred embodiment (shown in FIG. 4), the host apparatus 460 will not be described. The functional module card 610 according to the third preferred embodiment has such a configuration that the card controller 414, the communication section 415, the tuner section 111, and the demodulator 113 of the functional module card 410 according to the second preferred embodiment (see FIG. 4) are replaced with a card controller 614, a communication section 615, a tuner section 611, and a demodulator 613, respectively. The card controller 614 includes a TS receiver section 620, a buffer memory 621, a buffer controller 622, a communication section 615, a tuner section controller 116, and a card information storage section 117. The tuner section 611 transfers a TS and a TS clock generated by the demodulator 613 to the selector 420 and the TS receiver section 620. The other components that constitute the functional module card 610 are the same as those of the functional module card 410 according to the second preferred embodiment. Accordingly, the components as used commonly to the digital broadcasting receiver apparatuses according the second and the third preferred embodiments are denoted by the same reference numerals, respectively, and they will not be described.

The functional module card 610 and the host apparatus 460 are connected to each other via a bus 170. The bus 170 includes a clock line (or a data line) 131, a data line 132, a clock line 141, data lines 143 and 144, and a command/response line 142.

The communication section 615 of the functional module card 610 and the host apparatus 460 execute data transfer by use of a first data transfer method in response to a clock (a host clock) of the host apparatus 460. In the third preferred embodiment, the communication section 615 of the card controller 614 and the host controller 464 of the host apparatus 460 execute data transfer by use of the first data transfer method via the clock line 141, the command/response line 142, and one data line 143 (or two data lines 143 and 144 or four data lines 131, 132, 143, and 144).

When the switches 421, 422, 471, and 472 are switched over to broken line sides thereof, respectively (referred to as a "first data transfer mode"), the TS is transferred from the demodulator 613 of the functional module card 610 to the host controller 464 of the host apparatus 460 by use of a transfer method to be described later.

In the functional module card 610, an output buffer (not shown) of the tuner section 111 for outputting the TS and the TS clock, the communication section 615, and the selector 420 constitute a communication section of the functional module card 610. The tuner 112 and the demodulator 113 of the tuner section 611 constitute a broadcasting signal reception section.

Referring to FIGS. 3 and 5, the method for controlling the functional module card and the method for controlling the host apparatus according to the third preferred embodiment of the present invention will be described. FIG. 5 is a flowchart showing a digital broadcasting receiving method (including the method for controlling the functional module card and the method for controlling the host apparatus) according to the second preferred embodiment of the present invention, in particular showing the method for controlling the functional module card 610 and the method for controlling the host apparatus 460, from at the time when the user transmits a terrestrial digital broadcasting reception start command to the host apparatus 460 to the time when selectors 420 and 470 (the switches 421, 422, 471, and 472) are switched over. Since the method for controlling the functional module card 610 and the method for controlling the host apparatus 410 according to the third preferred embodiment shown in FIG. 5 are the same as those according to the second preferred embodiments, the methods will not be described.

When the host apparatus 460 permits the transfer of the TS using the second data transfer method, the transfer of the TS from the functional module card 610 to the host apparatus 460 is executed by the same method as that according to the first and the second preferred embodiments (shown in FIG. 3) (the switches 421, 422, 471, and 471 are switched over to the solid line sides thereof, respectively, and this state is referred to as a "second data transfer mode"). FIG. 3 is already described above.

When the host apparatus 460 does not permit the transfer of the TS using the second data transfer method (the first data transfer mode), the transfer of the TS from the functional module card 610 to the host apparatus 460 is executed as follows.

The TS receiver section 620 receives the TS and the TS clock from the demodulator 613, and transfers the TS to the buffer controller 622. The buffer controller 622 controls the buffer memory 621 so as to temporarily store the TS. The host controller 464 transfers the TS stored in the buffer memory 621 to the host controller 464 by use of a master-slave data transfer method in which the host apparatus 460 operates as a master apparatus. The TS is transmitted from the functional module card 610 to the host apparatus 460 by use of the first data transfer method described above (using the host clock as a synchronous transfer clock). The four lines of the clock line 131 and the data lines 132, 143, and 144 are used as data lines for the transfer of the TS. The buffer controller 622 reads the TS from the buffer memory and transmits a read TS to the host controller 464 in response to a TS transfer command that is transmitted from the host controller 464 via the command/response line 142 and the communication section 615.

The host controller 464 receives the TS, and transfers a received TS to the decoder and descrambler 163 in response to a command from a CPU 161. The decoder and descrambler 163 decodes and descrambles a TS packet and transfers video and audio signals to an input and output section 165. The input and output section 165 outputs the video and audio signals. When the TS is transferred from the functional module card 610 to the host apparatus 410 by use of the first data transfer method, the input and output section 165 outputs the video and audio signals at a timing of the host clock.

The CPU 161 monitors either a time interval of the TS clock or the number of TS clocks within a certain time interval based on a change in an amount of the TS stored in the buffer memory 621. When the time interval of the TS clock has become longer or the number of the TS clocks within the certain time interval has been decreased, the CPU 161 transmits a command to the decoder and descrambler 163, so as to instruct the decoder and descrambler 163 to decelerate an output rate of the video and audio signals to the input and output section 165. When the time interval of the TS clock has become shorter or the number of the TS clocks within the certain time interval has been increased, the CPU 161 transmits a command to the decoder and descrambler 163, so as to instruct the decoder and descrambler 163 to accelerate the output rate of the video and audio signal to the input and output section 165. By doing so, even if the host apparatus 460 does not permit transferring the TS using the second data transfer method, the TS can be transmitted from the functional module card 610 to the host apparatus 460. Although a video and audio signal output clock used in this transmission is not so correct as that in the TS transmission using the second data transfer method, the video and audio signals can be outputted without image (or a sound) blackout, freeze, or skipping.

The host apparatus 460 according to the third preferred embodiment includes the selector 470, and is configured to be able to select one TS data transfer method by switching over the switches 471 and 472. Alternatively, the host apparatus 460 may be a host apparatus that corresponds to only one transfer method. In this case, the functional module card 610 can transfer the TS by use of the data transfer method (the first data transfer method or the second data transfer method) designated by the host apparatus by switching over the switches 421 and 422 of the selector 420.

When the switches 421, 422, 471 and 472 are switched over to the broken line sides thereof, respectively (in the first data transfer mode), the tuner section 611 may be able to refrain from outputting the TS and the TS clock in response to a command from the CPU 161. When the tuner section 611 does not output the TS and the TS clock, operations of the functional module card 610 and the host apparatus 460 are identical to those of the functional module card 410 and the host apparatus 460 in the first data transfer mode according to the second preferred embodiment. They will not be described.

According to the above-described preferred embodiments, a signal inputted to the functional module card 110, 410 or 610 may be a BS digital broadcasting signal or a CS digital broadcasting signal.

The third preferred embodiment can exhibit the following advantageous effect. Even if the host apparatus corresponds to either the first data transfer method or the second data transfer method, it is possible to realize the digital broadcasting receiver apparatus that can executes both of the operation function (the first transfer method) such as a channel setting and the transfer of the TS (the first or the second transfer method), and the functional module card and the inexpensive host apparatus that constitutes the digital broadcasting receiver apparatus.

In the above-described preferred embodiment, the TS clock is transferred from the demodulator 613 to the decoder and descrambler 163 via the clock generator 166. Alternatively, the TS clock may be transferred from the demodulator 613 to the decoder and descrambler 163 without involvement of the clock generator 166.

The digital broadcasting signal may be encrypted instead of scrambled as described in the above-described preferred embodiments. In this case, the functional module card includes a tuner section, and the host apparatus includes a decoder and a decryption section. The functional module card may include the decoder.

The transport stream used in the above-described preferred embodiments may be replaced by a decoded or descrambled data signal (a data signal of the digital broadcasting signal). In this case, the functional module card includes a decoder or a decoder and descrambler.

In the digital broadcasting receiver apparatus that includes the functional module card and the host apparatus according to the present invention, the descrambler and the tuner section are separately installed into the functional module card and the host apparatus, respectively. The functional module card can directly output the TS and the clock (the TS clock) generated from the synchronous signal of the TS to a bus.

According to the present invention, it is advantageously possible to realize the digital broadcasting receiver apparatus capable of attaching, as an optional unit, the functional module card that includes the digital broadcasting reception function to the host apparatus, and the functional module card and the inexpensive host apparatus that constitutes the digital broadcasting receiver apparatus.

According to the present invention, it is advantageously possible to realize the functional module card that includes the versatile interface and the digital broadcasting signal reception function, and that transfers the digital broadcasting signal to the host apparatus in response to a correct clock, the host apparatus corresponding to the functional module card, the method for controlling the functional module card, and the method for controlling the host apparatus.

According to the present invention, it is advantageously possible to realize the functional module card capable of transferring data by use of the ordinary data transfer method even while the TS is transmitted from the functional module card to the host apparatus, the host apparatus corresponding to the functional module card, the method for controlling the functional module card, and the method for controlling the host apparatus.

The functional module card selects the transfer method for transferring the TS in response to the designation by the host apparatus, from (a) the first transfer method for transferring the TS in synchronization with a clock generated by the host apparatus and (b) the second transfer method for transferring the TS in synchronization with a clock generated from the synchronous signal of the TS. Accordingly, it is advantageously possible to realize the digital broadcasting receiver apparatus capable of including both the function (the first transfer method) such as the channel setting and the transfer of the TS (the first or the second transfer method) whichever transfer method the host apparatus corresponds to, and the functional module card and the inexpensive host apparatus that constitutes the digital broadcasting receiver apparatus.

According to the present invention, it is advantageously possible to realize the functional module card that includes the digital broadcasting reception function, that can be attached, as an optional unit, to the host apparatus, and that cannot normally output the digital broadcasting signals if the functional module card is not attached to the host apparatus of the user who pays charges to the broadcasting station, the inexpensive host apparatus corresponding to the functional module card, the method for controlling the functional module card, and the methods for controlling the host apparatus. It is advantageously possible to realize the inexpensive host apparatus that has high function extendability and that can protect copyrights of digital contents, the functional module card corresponding to the host apparatus, the method for controlling the functional module card, and the method for controlling the host apparatus.

Although the invention has been described in some detail dealing with the preferred embodiments, the configuration details of any of the preferred embodiments disclosed herein may be changed or modified, and any changes in the combination or order of components thereof can be accomplished without departing from the spirit and scope of the invention as set forth in the appended claims.

INDUSTRIAL APPLICABILITY

The functional module card, the host apparatus, the method for controlling the functional module card, and the method for controlling the host apparatus are useful as a functional module card and a host apparatus that constitute, for example, a digital broadcasting receiver apparatus, a method for controlling the functional module card, and a method for controlling the host apparatus, respectively.

The invention claimed is:

1. A functional module card comprising:
 a communication section for communicating with a host apparatus via a plurality of connection lines; and
 a broadcasting signal receiver section for receiving a digital broadcasting signal, generating a data signal of the digital broadcasting signals, and generating a clock for transferring the data signal based on a synchronous signal extracted from the data signal,
 wherein said communication section includes:
 a first data transfer mode for transferring data via a data bus of connection lines selected from the plurality of connection lines; and
 a second data transfer mode for transmitting the data signal and the clock for transferring the data signal, respectively, to the host apparatus via a first connection line and via at least one additional connection line other than the first connection line, the first connection line and the at least one additional connection line being selected from the connection lines which transfer the data in the first data transfer mode, and
 wherein, in the second data transfer mode, said communication section transfers the data signal synchronously with the clock for transferring the data signal.

2. The functional module card as claimed in claim 1, wherein the data signal is a transport stream.

3. The functional module card as claimed in claim 1, wherein said communication section further transfers data to the host apparatus in the second data transfer mode, using the same transfer protocol as a transfer protocol used in the first data transfer mode, and using a data bus having a number of lines smaller than that of the first transfer mode the data bus being selected in a further connection line other than the connection lines as used upon transferring the data signal and the clock for transferring the data signal in the second transfer mode, the further connection line being selected from the connection lines as used as the data bus in the first data transfer mode.

4. The functional module card as claimed in claim 1, wherein said communication section starts communicating with the host apparatus in the first data transfer mode upon being activated, and communicates with the host apparatus after switching over to the second data transfer mode upon receiving a command for switching over to the second data transfer mode from the host apparatus.

5. The functional module card as claimed in claim 1, further comprising a buffer memory for storing the data signal received by said broadcasting signal receiver section,
 wherein, responsive to a command from the host apparatus, said communication section selectively executes one of the following:
 transmitting the data signal received by said broadcasting signal receiver section to the host apparatus in the second data transfer mode; and
 storing the data signal in the buffer memory, reading the data signal from the buffer memory, and transmitting a read data signal to the host apparatus in the first data transfer mode.

6. The functional module card as claimed in claim 1, wherein the first data transfer mode, the data is transferred via the data bus of the connection lines selected from the plurality of connection lines by a master-slave communication in which the host apparatus operates as a master apparatus and said functional module card operates as a slave apparatus.

7. A host apparatus comprising:
 a communication section for communicating with a functional module card via a plurality of connection lines; and
 a broadcasting signal output section for inputting a data signal of a digital broadcasting signal and a clock for transferring the data signal, which are transmitted from the functional module card, for performing a predetermined processing on the data signal and the clock, and for outputting a resultant data signal and a resultant clock,
 wherein said communication section includes:
 a first data transfer mode for transferring data via a data bus of connection lines selected from the plurality of connection lines; and
 a second data transfer mode for inputting the data signal and the clock for transferring the data signal, respectively, to said host apparatus via a first connection line and via at least one additional connection line other than the first connection line, the first connection line and the at least one additional connection line being selected from the connection lines which transfer the data in the first data transfer mode,
 wherein the clock for transferring the data signal is generated based on a synchronous signal extracted from the data signal, and
 wherein, in the second data transfer mode, said communication section inputs the data signal synchronously with the clock for transferring the data signal.

8. The host apparatus as claimed in claim 7, wherein the data signal is a transport stream.

9. The host apparatus as claimed in claim 7, wherein said communication section further inputs data from the functional module card in the second data transfer mode, using the same transfer protocol as a transfer protocol used in the first data transfer mode, and using a data bus having a number of lines smaller than that of the first transfer mode, the data bus being selected in a further connection line other than the connection lines as used upon transferring the data signal and the clock for transferring the data signal in the second transfer mode, the further connection line being selected from the connection lines as used as the data bus in the first data transfer mode.

10. The host apparatus as claimed in claim 7, wherein said communication section starts communicating with the functional module card in the first data transfer mode upon being activated, and
 wherein when the functional module card receives the digital broadcasting signal and generates the data signal of the digital broadcasting signal and the clock for transferring the data signal, said communication section transmits a command to switch over to the second data transfer mode to the functional module card, switches over to the second data transfer mode, and thereafter communicates with the functional module card.

11. The host apparatus as claimed in claim 7, wherein in the first data transfer mode, the data is transferred via the data bus of the connection lines selected from the plurality of connection lines by a master-slave communication in which said host apparatus operates as a master apparatus and the functional module card operates as a slave apparatus.

12. A method for controlling a functional module card comprising:
- communicating with a host apparatus via a plurality of connection lines;
- receiving step of receiving a digital broadcasting signal, generating a data signal of the digital broadcasting signal; and
- generating a clock for transferring the data signal based on a synchronous signal extracted from the data signal,
- wherein said communicating comprises:
- a first data transfer mode for transferring data via a data bus of connection lines selected from the plurality of connection lines; and
- a second data transfer mode for transmitting the data signal and the clock for transferring the data signal, respectively, to the host apparatus via a first connection line and via at least one additional connection line other than the first connection line, the connection line and the at least one additional connection line being selected from the connection lines which transfer the data in the first data transfer mode, and
- wherein, in the second data transfer mode, said communicating further comprises transferring the data signal synchronously with the clock for transferring the data signal.

13. The method for controlling the functional module card as claimed in claim 12,
wherein the data signal is a transport stream.

14. The method for controlling the functional module card as claimed in claim 12,
wherein said communicating further comprises transferring data to the host apparatus in the second data transfer mode, using the same transfer protocol as a transfer protocol used in the first data transfer mode, and using a data bus having a number of lines smaller than that of the first transfer mode, the data bus being selected in a further connection line other than the connection lines as used upon transferring the data signal and the clock for transferring the data signal in the second transfer mode, the further connection line being selected from the connection lines as used as the data bus in the first data transfer mode.

15. The method for controlling the functional module card as claimed in claim 12,
wherein said communicating further comprises starting communication with the host apparatus in the first data transfer mode upon being activated, and communicating with the host apparatus after switching over to the second data transfer mode upon receiving a command for switching over to the second data transfer mode from the host apparatus.

16. The method for controlling the functional module card as claimed in claim 12,
wherein said communicating further comprises transmitting the data signal generated from the received digital broadcast signal to the host apparatus in one of the first data transfer mode and the second data transfer mode, responsive to a command from the host apparatus.

17. The method for controlling the functional module card as claimed in claim 12,
wherein in the first data transfer mode, the data is transferred via the data bus of the connection lines selected from the plurality of connection lines by a master-slave communication in which the host apparatus operates as a master apparatus and the functional module card operates as a slave apparatus.

18. A method for controlling a host apparatus comprising communicating with a functional module card via a plurality of connection lines;
- inputting a data signal of a digital broadcasting signal and a clock for transferring the data signal, which are transmitted from the functional module card;
- performing a predetermined processing on the data signal and the clock; and
- outputting a resultant data signal and a resultant clock,
- wherein said communicating comprises:
- a first data transfer mode for transferring data via a data bus of connection lines selected from the plurality of connection lines; and
- a second data transfer mode for inputting the data signal and the clock for transferring the data signal, respectively, to the host apparatus via a first connection line and via at least one additional connection line other than the first connection line, the first connection line and the at least one additional connection line being selected from the connection lines which transfer the data in the first data transfer mode,
- wherein the clock for transferring the data signal is generated based on a synchronous signal extracted from the data signal, and
- wherein, in the second data transfer mode, said communicating further comprises inputting the data signal synchronously with the clock for transferring the data signal.

19. The method for controlling the host apparatus as claimed in claim 18,
wherein the data signal is a transport stream.

20. The method for controlling the host apparatus as claimed in claim 18,
wherein said communicating further comprises inputting data from the functional module card in the second data transfer mode, using the same transfer protocol as a transfer protocol used in the first data transfer mode, and using a data bus having a number of lines smaller than that of the first transfer mode the data bus being selected in a further connection line other than the connection lines as used upon transferring the data signal and the clock for transferring the data signal in the second transfer mode, the further connection line being selected from the connection lines as used as the data bus in the first data transfer mode.

21. The method for controlling the host apparatus as claimed in claim 18,
wherein said communicating further comprises:
starting communication with the functional module card in the first data transfer mode upon being activated, and
when the functional module card receives the digital broadcasting signal and generates the data signal of the digital broadcasting signal and the clock for transferring the data signal, transmitting a command to switch over to the second data transfer mode to the functional module card, switching over to the second data transfer mode, and thereafter communicating with the functional module card.

22. The method for controlling the host apparatus as claimed in claim 18,
wherein in the first data transfer mode, the data is transferred via the data bus of the connection lines selected from the plurality of connection lines by a master-slave communication in which the host apparatus operates as a master apparatus and the functional module card operates as a slave apparatus.

* * * * *